US009187549B2

(12) United States Patent
Krarup et al.

(10) Patent No.: US 9,187,549 B2
(45) Date of Patent: Nov. 17, 2015

(54) REDUCTION OF THE CONTENT OF PROTEIN CONTAMINANTS IN COMPOSITIONS COMPRISING A VITAMIN K-DEPENDENT PROTEIN OF INTEREST

(75) Inventors: Janus Krarup, Gentofte (DK); Thomas Budde Hansen, Copenhagen (DK); Anne Charlotte Arentsen, Holte (DK); Daniel E. Rasmussen, Copenhagen (DK); Are Bogsnes, Nivå (DK); Arne Staby, Bagsværd (DK); Haleh Ahmadian, Solrød Strand (DK); Susanne Bang, Bagsværd (DK)

(73) Assignee: Novo Nordisk Healthcare A/G, Zurich (CH)

( * ) Notice: Subject to any disclaimer, the term of this patent is extended or adjusted under 35 U.S.C. 154(b) by 799 days.

(21) Appl. No.: 11/722,644

(22) PCT Filed: Dec. 23, 2005

(86) PCT No.: PCT/EP2005/057145
§ 371 (c)(1),
(2), (4) Date: Jan. 16, 2008

(87) PCT Pub. No.: WO2006/067230
PCT Pub. Date: Jun. 29, 2006

(65) Prior Publication Data
US 2008/0207880 A1 Aug. 28, 2008

Related U.S. Application Data

(60) Provisional application No. 60/641,256, filed on Jan. 4, 2005.

(30) Foreign Application Priority Data

Dec. 23, 2004 (DK) .................................. 2004 02008

(51) Int. Cl.
C07K 1/14 (2006.01)
C07K 1/22 (2006.01)
C07K 14/745 (2006.01)
A61K 38/36 (2006.01)
C07K 16/36 (2006.01)
C07K 1/16 (2006.01)

(52) U.S. Cl.
CPC ............... *C07K 14/745* (2013.01); *C07K 1/16* (2013.01); *C07K 1/22* (2013.01)

(58) Field of Classification Search
None
See application file for complete search history.

(56) References Cited

U.S. PATENT DOCUMENTS

| 4,721,572 A | 1/1988 | Jordan |
| 5,055,557 A | 10/1991 | Zimmerman |
| 5,633,350 A | 5/1997 | Fischer et al. |
| 5,700,914 A | 12/1997 | Jorgensen |
| 5,753,123 A | 5/1998 | Kajihara et al. |
| 5,932,706 A | 8/1999 | Mertens et al. |
| 2002/0045240 A1 | 4/2002 | Josic et al. |
| 2003/0138844 A1 | 7/2003 | Stenflo et al. |

FOREIGN PATENT DOCUMENTS

| AU | 2005/318106 A1 | 6/2006 |
| EP | 363126 A2 | 4/1990 |
| EP | 118256 | 5/1992 |
| EP | 496725 | 12/1996 |
| EP | 669342 | 9/2001 |
| JP | 63-148994 A | 6/1988 |
| JP | 1-231893 A | 9/1989 |
| JP | 7-258286 | 10/1995 |
| JP | 9-110900 | 4/1997 |
| JP | 9-506256 | 6/1997 |
| JP | 2824430 B2 | 11/1998 |
| JP | 2000-143692 A | 5/2000 |
| JP | 2000511407 A | 9/2000 |
| JP | 2001-247599 | 9/2001 |
| WO | 9516030 A1 | 6/1995 |
| WO | 9740145 A1 | 10/1997 |
| WO | WO 00/55203 | 9/2000 |
| WO | WO 02/22776 | 3/2002 |
| WO | 0229045 A2 | 4/2002 |
| WO | WO 0229045 A2 * | 4/2002 |
| WO | 03/029442 A1 | 4/2003 |
| WO | 031027147 A2 | 4/2003 |

OTHER PUBLICATIONS

Di Scipio, R.G., et al. 1977 Biochemistry 16(4): 698-706.*
Dahlback, B., et al. 1990 The Journal of Biological Chemistry 265(14): 8127-8135.*
Office Action in U.S. Appl. No. 11/807,558, sent from the USPTO on Apr. 13, 2009.
Final Office Action mailed May 12, 2009 in U.S. Appl. No. 11/358,676, filed Feb. 21, 2006 by Hansen.
Jenny R. et al., Preparative Biochemistry, vol. 16(3), pp. 227-245 (1986).
Tharakan, J. et al., Vox Sanguinis, vol. 58, pp. 21-29 (1990).

(Continued)

*Primary Examiner* — Marsha Tsay
(74) *Attorney, Agent, or Firm* — Nonna G. Akopyan

(57) ABSTRACT

The present invention relates to Vitamin K-dependent protein compositions having a very low, or negligible, content of protein contaminants. The present invention also relates to method applicable in the preparation of such Vitamin K-dependent protein compositions. Such methods may either be used alone or in sequential combination with the purpose of reducing the relative content of protein contaminants. The present invention is particularly relevant in the preparation of compositions of coagulation factors selected from Factor X polypeptides (FX/FXa), Factor IX polypeptides (FIX/FIXa), Factor VII polypeptides (FVII/FVIIa), and the anticoagulant Protein C, in particular Factor VII polypeptides.

2 Claims, No Drawings

(56) References Cited

OTHER PUBLICATIONS

Stenberg, L.M. et al., Biochemical and Biophysical Research Communications, vol. 283, pp. 454-459 (2001).
Wu, H. et al., Advances in Experimental Medicine and Biology, vol. 530, pp. 143-151 (2003).
Nelsesetuen, G. et al., Journal of Biological Chemistry, vol. 251(22), pp. 6886-6893 (1976).
Furie, B. et al., Journal of Biological Chemistry, vol. 253(24), pp. 8980-8987 (1978).
Yan, S. Betty, Journal of Molecular Recognition, vol. 9, pp. 211-218 (1996).
Bjorn, S. et al., Research Disclosure, vol. 9, p. 26960 (1986).
Yan, S.C.B. et al., Biotechnology, vol. 8, pp. 655-661 (1990).
Furie, B. et al., Journal of Biological Chemistry, vol. 254(19), pp. 9766-9771 (1979).
Church, W.R. et al., Journal of Biological Chemistry, vol. 263(13), pp. 6259-6267 (1988).
Brown, M.A. et al., Journal of Biological Chemistry, vol. 275(26), pp. 19795-19802 (2000).
Harvey et al., "Mutagenesis of the γ-Carboxyglutamic Acid Domain of Human Factor VII to Generate Maximum Enhancement of the Membrane Contact Site", Journal of Biological Chemistry, 2003, vol. 278, No. 10, pp. 8363-8369.
Suomela, "Human Coagulation Factor IX", European Journal of Biochemistry, 1976, vol. 71, pp. 145-154.
Abstract of JP 2001-247599, dated Sep. 11 2001, Fujimori Kogyo Co.
Poser, JW et al. Isolation and Sequence of the Vitamin K-Dependent protein from Human Bone. Undercarboxylation of the First Glutamic Acid Residue, The Journal of Biological Chemistry. 1980. vol. 255(18). pp. 8865-8869.
Liebman HA et al; Immunoaffinity purification of factor IX (Christmas factor) by using conformation-specific antibodies directed against the factor IX-metal complex, Journal Proc Natl Acad Sci U S A. Year Jun. 1985; vol. 82(11):pp. 3879-3883.

\* cited by examiner

REDUCTION OF THE CONTENT OF PROTEIN CONTAMINANTS IN COMPOSITIONS COMPRISING A VITAMIN K-DEPENDENT PROTEIN OF INTEREST

CROSS-REFERENCE TO RELATED APPLICATIONS

This application is a 35 U.S.C. §371 national stage application of International Patent Application PCT/EP2005/057145 (published as WO 2006/067230), filed Dec. 23, 2005, which claimed priority of Danish Patent Application PA 2004 02008, filed Dec. 23, 2004; this application further claims priority under 35 U.S.C. §119 of U.S. Provisional Application 60/641,256, filed Jan. 4, 2005.

FIELD OF THE INVENTION

The present invention relates to Vitamin K-dependent protein compositions having a very low, or negligible, content of protein contaminants. The present invention also relates to method applicable in the preparation of such Vitamin K-dependent protein compositions. Such methods may either be used alone or in sequential combination with the purpose of reducing the relative content of protein contaminants. The present invention is particularly relevant in the preparation of compositions of coagulation factors selected from Factor X polypeptides (FX/FXa), Factor IX polypeptides (FIX/FIXa), Factor VII polypeptides (FVII/FVIIa), and the anticoagulant Protein C, in particular Factor VII polypeptides.

BACKGROUND OF THE INVENTION

In the production of recombinant proteins from cultures of microorganisms or cell lines, the final production step is the recovery and optionally the concentration of the product of interest. Culture media in which the cells have been grown and which contain secreted proteins, and, in particular, cell lysates containing intracellular proteins of interest also contain, to a greater or lesser extent, other proteins produced by the cells, apart from other contaminants, such as media components, nucleic acids and the like. In order to obtain a purified protein product, it is therefore necessary to separate the protein of interest from other proteins and polypeptides and other impurities in the crude material containing the protein of interest.

It is often difficult to remove protein contaminant comprising domains of the same nature as the polypeptide of interest.

Vitamin K-dependent proteins are distinguished from other proteins by sharing a common structural feature in their amino terminal part of the molecule. The N-terminal of these proteins, also referred to as the Gla-domain, is rich in the unusual amino acid γ-carboxy glutamic acid which is synthesized from glutamate in a Vitamin K-dependent reaction catalysed by the enzyme γ-glutamyl carboxylase. Because of the presence of about 2 to 12 Gla residues, the Gla-domain is characterised by being capable of binding divalent cations such as $Ca^{2+}$. Upon binding of metal ions, these proteins undergo conformational changes which can be measured by several techniques such as circular dichroism and fluorescence emission.

The discovery of metal induced conformational changes of Gla-containing proteins (Nelsestuen et. al., J. Biol. Chem. 1976; 251, 6886-6893) together with identification of conformation specific polyclonal antibodies (Furie et al., J. Biol. Chem. 1978; 253, 8980-8987) opened the way for the introduction of conformation specific immunoaffinity chromatography. These antibodies could recognise and bind the Gla-domain in the presence of $Ca^{2+}$ ions but released the protein upon removal of $Ca^{2+}$ ions using a $Ca^{2+}$ chelator such as EDTA or citrate.

In the 1980's conformation specific pseudoaffinity chromatography was developed making use of the unique property of Gla containing proteins to undergo metal induced changes in conformation. Pseudoaffinity chromatography differs from the conventional affinity chromatography in that there is no immobilized affinity ligand involved and it is performed on a conventional chromatographic matrix (Yan S. B., J. Mol. Recog. 1996; 9, 211-218). The Gla protein can be adsorbed to an anion exchange material by eliminating divalent metal ions. Subsequently, elution is performed by adding $Ca^{2+}$ to the elution buffer.

In 1986, Bjørn and Thim reported purification of recombinant Factor VII on an anion exchange material taking advantage of $Ca^{2+}$-binding property of Gla-domain of Factor VII (Bjørn S. and Thim L., Research Disclosure, 1986, 26960-26962.). Adsorption was achieved in a buffer without $Ca^{2+}$ and elution of Factor VII was possible using a $Ca^{2+}$ containing buffer with low ionic strength and under mild conditions.

Yan et al. have used the same principle for the purification of recombinant human Protein C (Yan S. B. et al., Bio/technology. 1990; 8, 655-661).

While the presence of Gla-domain provides an advantage for separation of Gla containing proteins from other proteins, the inventors of present invention observed that similar properties and behaviour of the Gla containing proteins makes it difficult to separate them from each other. Several conformational specific antibodies raised against one Gla proteins show cross reactivity with other Gla proteins (Furie B. and Furie B., J. Biol. Chem. 1979; 254, 9766-9771; Church et al., J. Biol. Chem. 1988; 263, 6259-6267.).

Brown et al. (Brown et al., J. Biol. Chem. 2000; 275, 19795-19802.) have reported monoclonal antibodies specific for Gla residues. These antibodies could recognize all of the Gla proteins tested: Factor VII, Factor IX, Factor II, Protein C, Protein S, GAS-6, bone matrix Gla protein, conantokin G.

Proteins with a GLA-domain comprises, but is not limited to, the following proteins: GAS-6, Protein S, Factor II (Prothrombin), thrombin, Factor X/Xa, Factor IX/IXa, Protein C, Factor VII/VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin.

U.S. Pat. No. 5,633,350 describes a method for the separation of Vitamin K dependent proteins from non-Vitamin K dependent accompanying proteins.

The need for efficiently separating a Vitamin K-dependent protein of interest, such as a Gla-domain containing polypeptide of interest, from protein contaminants is a particularly relevant issue when dealing with the purification of such polypeptides produced in cell cultures, because the host cell (which may not be a human cell line) may produce significant amounts of protein contaminants that can cause undesirable immunogenic reactions upon use of the polypeptide.

Thus, an object of the present invention is to provide suitable methods for the reduction or even removal of the content of protein contaminants in compositions comprising a Vitamin K-dependent protein of interest. A further object of the present invention is to provide compositions comprising a Vitamin K-dependent protein of interest with a very low or even negligible content of protein contaminants.

DESCRIPTION OF THE INVENTION

The invention relates to various methods for reducing or even eliminating the content of protein contaminant(s) in compositions comprising a Vitamin K-dependent protein of interest.

Vitamin K-Dependent Proteins of Interest

The present invention relates in a broad aspect to the purification of a Vitamin K-dependent protein of interest and to particular purified compositions comprising such proteins. The term "of interest" is applied herein as a pointer to the particular species (a Vitamin K-dependent protein) which is relevant to obtain in the most pure form, e.g. for the purpose of using the Vitamin K-dependent protein in a therapeutic context.

The methods described herein may in principle be applicable to the purification of any Vitamin K-dependent protein comprising, but not limited to, GAS-6, Protein S, Factor II (Prothrombin), Thrombin, Factor X/Xa, Factor IX/IXa, Protein C, Factor VII/VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin), in particular Vitamin K-dependent coagulation factors selected from Factor VII polypeptides, Factor IX polypeptides, Factor X polypeptides and activated Protein C. In one particular embodiment, the method is used for the purification of recombinant Vitamin K-dependent proteins of interest produced under cell culture conditions, in particular non-human cell cultures.

In one particular embodiment, the Vitamin K-dependent protein of interest is a Factor IX polypeptide, such as FIX or FIXa.

In another particular embodiment, the Vitamin K-dependent protein of interest is a Factor VII polypeptide, such as a Factor VII-related polypeptide, or a Factor VII derivatives, or a Factor VII conjugate, in particular a human Factor VII polypeptide, in particular human wild type Factor VII or wild type human Factor VIIa.

As used herein, the terms "Factor VII polypeptide" and "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes Factor VII variants, Factor VII-related polypeptides, Factor VII derivatives and Factor VII conjugates exhibiting substantially the same or improved biological activity relative to wild-type human Factor VIIa.

The terms "Factor VII" or "FVII" are intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "wild type human Factor VIIa" is a polypeptide having the amino acid sequence disclosed in U.S. Pat. No. 4,784,950.

As used herein, "Factor VII-related polypeptides" encompasses polypeptides, including variants (or analogues), in which the Factor VIIa biological activity has been substantially modified, such as reduced, relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate a Factor VII polypeptide exhibiting substantially the same or improved biological activity relative to wild-type Factor VII, in which one or more of the amino acids of the parent peptide have been genetically and/or chemically and/ or enzymatically modified, e.g. by alkylation, glycosylation, PEGylation, GlycoPEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated Factor VII derivatives as disclosed in WO 03/31464 and US Patent applications US 20040043446, US 20040063911, US 20040142856, US 20040137557, and US 20040132640 (Neose Technologies, Inc.); Factor VII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to Factor VII polypeptides with i) substantially the same or increased proteolytic activity compared to recombinant wild type human Factor VIIa or ii) to Factor VII polypeptides with substantially the same or increased TF binding activity compared to recombinant wild type human Factor VIIa or iii) to Factor VII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-Factor VIIa, S60A-Factor VIIa (Lino et al., Arch. Biochem. Biophys. 352: 182-192, 1998); Factor VIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); Factor VII variants as disclosed in PCT/DK02/00189 (corresponding to WO 02/077218); and Factor VII variants exhibiting increased proteolytic stability as disclosed in WO 02/38162 (Scripps Research Institute); Factor VII variants having a modified Gla-domain and exhibiting an enhanced membrane binding as disclosed in WO 99/20767, U.S. patent 60/17882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693, 075 (University of Minnesota); and Factor VII variants as disclosed in WO 01/58935, U.S. Pat. No. 6,806,063, US patent application 20030096338 (Maxygen ApS), WO 03/93465 (Maxygen ApS) and WO 04/029091 (Maxygen ApS).

Non-limiting examples of Factor VII variants having increased biological activity compared to wild-type Factor VIIa include Factor VII variants as disclosed in WO 01/83725, WO 02/22776, WO 02/077218, PCT/DK02/00635 (corresponding to WO 03/027147), Danish patent application PA 2002 01423 (corresponding to WO 04/029090), Danish patent application PA 2001 01627 (corresponding to WO 03/027147); WO 02/38162 (Scripps Research Institute); and Factor VIIa variants with enhanced activity as disclosed in JP 2001061479 (Chemo-Sero-Therapeutic Res Inst.).

Examples of variants of factor VII include, without limitation, P10Q-FVII, K32E-FVII, P10Q/K23E-FVII, L305V-FVII, L305V/M306D/D309S-FVII, L305T-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/K316Q/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/S314E-FVII, F374Y/L305V/M298Q/V158T-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158D/E296V/S314E-FVII, F374Y/V158T/E296V/

M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L305I, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

The expression "polypeptides" in connection with the terms "Factor X polypeptides" and "Factor IX polypeptides" is intended to encompass any protein comprising the amino acid sequence of the wild-type human Factor X and Factor IX, respectively, as well as the respective "analogues", "variants", "related polypeptides", "derivatives" and "conjugates" thereof, where the expressions "variants", "related polypeptides", "derivatives" and "conjugates" are defined as for Factor VII, mutatis mutandis.

Compositions

When used herein, the expression "composition" is intended to mean a liquid composition, such as an aqueous liquid composition, i.e. a composition comprising less than 5% of non-aqueous solvents.

The term "first composition" refers to a composition comprising a Vitamin K-dependent protein of interest prior to a treatment, such as a purification step, according to the present invention. The term is used to distinguish the "first composition" from "a second composition", which refers to the same composition, but after such treatment, such as a purification step.

The Vitamin K-dependent protein of interest is most typically a recombinant protein produced under cell culture conditions, i.e. the Vitamin K-dependent protein of interest is either obtained directly as a constituent of a cell culture supernatant, or obtained from a cell culture supernatant after one or more preceding process steps. In practising the present invention, the cells are eukaryote cells, such as an established eukaryote cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. A preferred CHO cell line is the CHO K1 cell line available from ATCC under accession number CCl61.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77:4216-4220, 1980) (DUKX cells also being referred to as DXB11 cells), and DG44 (CHO cell line) (Cell, 33: 405, 1983, and *Somatic Cell and Molecular Genetics* 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. Suitable insect cell lines also include, without limitation, *Lepidoptera* cell lines, such as *Spodoptera frugiperda* cells or *Trichoplusia ni* cells (see, e.g., U.S. Pat. No. 5,077,214).

Typically, the total content of protein contaminants in the first (such as an unpurified) composition is at least 200 ppm, such as at least 300 ppm, e.g. at least 400 ppm, or at least 500 ppm.

Also typically, the total content of Protein S contaminants in the first (such as an unpurified) composition is at least 200 ppm, such as at least 300 ppm, e.g. at least 400 ppm, or at least 500 ppm.

Typical Protein Contaminants

When used herein, the terms "protein contaminant" and "protein contaminants" and the like are intended to refer to protein or polypeptide constituents constituting impurities in relation to the Vitamin K-dependent protein of interest. Thus, the Vitamin K-dependent protein of interest will obviously not be counted as a protein contaminant although the definitions of "Vitamin K-dependent protein" as such and "protein contaminants", respectively, are partly overlapping. In one embodiment the protein contaminant is a Vitamin K-dependent protein (but not the Vitamin K-dependent protein of interest).

As the Vitamin K-dependent proteins are typically produced in cell cultures, a particular groups of protein contaminants is host cell proteins. "Host cell proteins" are proteins produced by the host cell expressing the Vitamin K-dependent protein of interest, and are typically considered as impurities. Host cell proteins can be human proteins if a human cell line is used for production of Vitamin K-dependent protein of interest or non-human proteins, if a non-human cell line is used for production of the protein of interest. Thus, in one aspect of the invention, the protein contaminant is a host cell protein, such as a Vitamin K-dependent protein.

A particularly relevant class of host cell proteins are Gla-domain containing proteins such as GAS-6, Protein S, Factor II (Prothrombin), thrombin, Factor X/Xa, Factor IX/IXa, Protein C, Factor VII/VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin. The number of Gla residue in these proteins is in the range of 2-12. Since the synthesis of Gla residues requires Vitamin K, proteins containing Gla residues are also referred to as Vitamin K-dependent proteins.

In the present context, a particular host cell protein of relevance is Protein S. In a particular embodiment the Protein S is a hamster Protein S. Thus, the methods and compositions defined herein are particularly focussed on the reduction of the content of Protein S.

Reduction of Content of Protein Contaminants

A pivotal aspect of the present invention is the method(s) capable of removing protein contaminant (in particular Protein S) from compositions comprising a Vitamin K-dependent protein of interest (in particular a Factor VII polypeptide).

Thus, the present invention relates to a method for reducing the content of one or more protein contaminants in a composition comprising a Vitamin K-dependent protein of interest, said method comprising at least the steps of (i) contacting the composition with a solid phase material which is able to bind the one or more protein contaminants and/or the Vitamin K-dependent protein of interest, and (ii) collecting a resulting composition comprising the Vitamin K-dependent protein of interest, whereby the level of protein contaminant(s) expressed as parts per million relative to the Vitamin K-dependent protein of interest has been reduced by at least a factor of 5.

In the most important embodiments, the total content of protein contaminants in the resulting second (such as a purified) composition comprising the Vitamin K-dependent protein of interest is brought down to at the most 100 ppm.

As mentioned above, the Vitamin K-dependent protein of interest is typically a Vitamin K-dependent coagulation factor selected from Factor VII polypeptides, Factor IX polypeptides, Factor X polypeptides and activated Protein C. In one more particular embodiment, the Vitamin K-dependent protein of interest is a Factor IX polypeptide. In another more particular embodiment, the Vitamin K-dependent protein of interest is a Factor VII polypeptide. In another particular embodiment, the Vitamin K-dependent protein of interest is a Factor X polypeptide.

In a particular embodiment, the predominant amount of protein contaminants are Gla-domain containing polypeptides, in particular Protein S; and the Vitamin K-dependent protein of interest is a Factor VII polypeptide. In one embodiment, the protein contaminant is hamster protein S. In another embodiment, the protein contaminant is protein S and the Vitamin K-dependent protein of interest is a Factor IX polypeptide. In one embodiment, the protein contaminant is hamster protein S.

In one embodiment, the invention relates to methods for separation of a Vitamin K-dependent protein of interest containing 2-16 Gla-residues from other vitamin K-dependent protein contaminants containing 2-16 Gla-residues.

In another embodiment, the invention provides a method for separation of proteins with anti-coagulant effect such as protein S and protein C from proteins with coagulant effect. In one aspect, the Vitamin K-dependent protein of interest is a coagulation factor and the protein contaminant with anti-coagulant effect is Protein S.

In another embodiment, the invention provides a method for separation of non-human protein contaminants from human Vitamin K-dependent protein. In one aspect of the invention, the non-human protein contaminants are also Vitamin K-dependent proteins. In yet another aspect, the non-human protein contaminants are hamster proteins.

This being said, the method of the invention renders it possible to yield a level of protein contaminant(s) expressed as parts per million relative to the Vitamin K-dependent protein of interest which has been reduced by at least a factor of 10, or at least a factor of 25, or at least a factor of 50, such as by at least a factor of 100, or at least a factor of 250, or at least a factor of 500, or at least a factor of 750, or at least a factor of 1000, or at least a factor of 2000.

In particular, the total content of protein contaminants in the resulting second (such as a purified) composition, such as a treated cell culture supernatant, is at the most 100 ppm, such as at the most 90 ppm, or at the most 80 ppm, or at the most 70 ppm, or at the most 60 ppm, or at the most 50 ppm, or at the most 40 ppm, or at the most 30 ppm, or at the most 20 ppm, or at the most 10 ppm or at the most 5 ppm; or the total content of Protein S contaminants in the resulting second (such as a purified) composition, such as a treated cell culture supernatant, is at the most 100 ppm, such as at the most 90 ppm, or at the most 80 ppm, or at the most 70 ppm, or at the most 60 ppm, or at the most 50 ppm, or at the most 40 ppm, or at the most 30 ppm, or at the most 20 ppm, or at the most 10 ppm or at the most 5 ppm or at the most 1 ppm.

Typical cell culture supernatants may have a significant amount of protein contaminants (in particular Protein S), thus, the total content of protein contaminants in the (such as an unpurified) cell culture supernatant is typically at least 500 ppm, such as at least 750 ppm, or at least 1000 ppm, or at least 2000 ppm; or the total content of Protein S contaminants in the (such as an unpurified) cell culture supernatant is at least 500 ppm, such as at least 750 ppm, or at least 1000 ppm, or at least 2000 ppm.

Thus, in one aspect of the above relates to a method for reducing the content of one or more Protein S contaminants in a composition comprising a Factor VII polypeptide, said method comprising at least the steps of (i) contacting the composition with a solid phase material which is able to bind the Protein S contaminant(s) and/or the Factor VII polypeptide, and (ii) collecting a resulting composition comprising the Factor VII polypeptide, whereby the level of Protein S contaminant(s) expressed as parts per million relative to the Factor VII polypeptide has been reduced by at least a factor of 2, such as at least a factor of 5.

Solid phase materials useful herein are those typically used in chromatographic and affinity capture methods and processes and particular variants hereof, as will be evident.

In one main variant of the above, the solid phase material binds a relatively higher amount of the protein contaminant compared to the Vitamin K-dependent protein of interest. In one aspect, the Vitamin K-dependent protein of interest does not bind to the solid phase and flows through the chromatographic column while the protein contaminant binds to the solid phase, resulting in the separation of the Vitamin K-dependent protein of interest from the protein contaminant. In particular, the solid phase material specifically binds at least one of the contaminants, e.g. by strong affinity or by covalent binding of said contaminant(s), such as by formation of disulphide bonds to thiol moieties of said contaminant(s).

In one embodiment, the solid phase material is an ion exchange resin, such as anion exchange resin. Commonly used anion exchange resins comprises Q-resin, a Quaternary amine, and DEAE resin, DiEthylAminoEthane. Anion exchange resins are commercially available, e.g. Mono Q (Amersham Biosciences), Source 15Q or 30Q (Amersham Biosciences), Poros 20HQ or 50HQ (Perseptive Biosystems), Toyopearl Q650S (Toso Haas) and others.

The elution from the anion exchange resin can be performed by increasing the conductivity of the elution buffer such as increasing the concentration of the salts in the elution buffer, or by decreasing the pH of the elution buffer. In one particular embodiment of the invention the elution is performed by increasing the concentration of $CaCl_2$. In another particular embodiment the elution is performed by increasing the concentration of $MgCl_2$. The elution can be carried out stepwise or by using a gradient elution.

The most widely used cation exchange resin contains a carboxymethyl (CM) or sulfopropyl (SP) group. Examples of such cation exchangers include without limitation Toyopearl CM-650 or Toyopearl SP-650 (Toso Haas), Source 15 S or 30 S, CM or SP Sepharose Fast Flow (Amersham Biosciences) Obelix (Amersham Biosciences).

In another embodiment, the solid phase material is a matrix substituted with hydrophobic ligands such as ethyl-, butyl-, phenyl or hexyl-groups. This type of chromatography is referred to as hydrophobic interaction chromatography (HIC) and takes advantage of the hydrophobic properties of the proteins. The adsorption is promoted by the hydrophobic interactions between non-polar regions on the protein and immobilised hydrophobic ligands on a solid support. Adsorption is achieved at high salt concentrations in the aqueous mobile phase and elution is facilitated by decreasing the salt concentration. In one particular embodiment, material is a matrix substituted with a butyl or a phenyl ligand.

In a further aspect of the invention, the solid phase material carries affinity ligands. In one embodiment, the solid phase material is carrying monoclonal antibodies raised against at least one of the protein contaminant(s), in particular against Protein S. This is illustrated in the "Experimentals" section. In another aspect, the solid phase material is carrying immobilized triazine ligands, such as a triazane ligand as described in WO 97/10887 (such as a triazane ligand as described on page 5 lines 21 to page 13 line 6) or in U.S. Pat. No. 6,117,996 (such as paragraph 4-21) the content of which is hereby incorporated by reference in its entirety.

Protein S circulates in plasma either free or in complex with C4 bp. The B chain contains the interaction site for protein S. It is thus important for the present invention to use C4 bp species containing the B chain. In one embodiment of the invention the entire C4 bp molecule is used for immobilisation to the solid matrix. In another embodiment the B-chain or a sequence of B chain which is capable of binding protein S is used for immobilisation to the solid matrix.

In another variant, the solid phase material is carrying immobilised Protein C. In another variant, the solid phase material is carrying an immobilised triazin ligand. In another variant, the solid phase material is carrying C4 binding protein. Protein S binds to Protein C and C4 bp with much greater affinity than other Vitamin K-dependent proteins. It is therefore possible to reduce the content of Protein S by binding Protein S to immobilized Protein C or C4 bp. Alternatively, selected sequences of Protein C and C4 bp responsible for binding to Protein S can be used for immobilization to the solid phase.

The C4b-binding protein (C4 bp) is involved in the regulation of the complement system. It is a multimeric protein comprising 7 identical alpha chains and a single beta chain. The alpha and beta chains have molecular weights 70 kD and 45 kD, respectively. Both subunits belong to a superfamily of proteins composed predominantly of tandemly arranged short consensus repeats (SCR) approximately 60 amino acid residues in length.

In another embodiment, the solid phase material binds at least one of the contaminant(s) by covalent capture. Protein S has one free cysteine moiety, whereas Factor VII has none. The free cysteine moiety can then be attached selectively to an activated thiolated substance or a matrix by thiol-disulphide exchange, with the formation of a mixed disulphide. Hereby it should be possible to reduce Protein S by for example covalent chromatography, size exclusion chromatography or membrane processes. It should be understood that a variant of this embodiment is the one where a solid phase material is not involved, i.e. where disulphide formation (e.g. by the formation of dimers) renders it possible to separate the protein contaminant from the Vitamin K-dependent protein of interest by other means, e.g. by size exclusion chromatography or membrane processes.

In one particular embodiment, the Vitamin K-dependent protein of interest is a constituent of a cell culture supernatant, cf. the "Experimentals" section.

In another embodiment of the method defined further above, the solid phase material binds a relatively higher amount of the Vitamin K-dependent protein of interest compared to the protein contaminant(s). More particularly, the solid phase material specifically binds the Vitamin K-dependent protein of interest.

In one variant, the solid phase material is carrying monoclonal antibodies raised against the Vitamin K-dependent protein of interest or an analogue thereof.

In another variant, the solid phase material is carrying an inhibitor for said Vitamin K-dependent protein of interest, e.g. a benzamidine- or a guanidine-type inhibitor such as those comprising a $-C(=N-Z^1-R^1)-NH-Z^2-R^2$ motif, wherein $Z^1$ and $Z^2$ independently are selected from the group consisting of $-O-$, $-S-$, $-NR^H-$ and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or $Z^2$ and $R^2$ are as defined above and $-C=N-Z^1-R^1$ forms part of a heterocyclic ring, or $Z^1$ and $R^1$ are as defined above and $-C-NH-Z^2-R^2$ forms part of a heterocyclic ring, or $-C(=N-Z^1-R^1)-NH-Z^2-R^2$ forms a heterocyclic ring wherein $-Z^1-R^1-R^2-Z^2-$ is a biradical.

In still other variants, the solid phase material is carrying a metal which is capable of chelating with said Vitamin K-dependent protein of interest (where subsequent elution can be performed by pH change or with a buffer like imidazole), or is carrying immobilized tissue factor (thromboplastin) (in this instance it is found that Factor VII polypeptides binds to tissue factor with much greater affinity than protein contaminants like Protein S, for what reason it will be possible to reduce the content of, e.g., Protein S by binding, e.g., a Factor VII polypeptide to immobilized tissue factor (see also U.S. Pat. No. 6,573,056)), or is carrying immobilized heparin (see the "Experimentals" section), or is carrying phosphatidylserine (phosphatidylserine binds to the Gla-domain of Gla-domain comprising proteins like Vitamin K-dependent proteins only in the absence of calcium; in the presence of calcium, phosphatidylserine bind to the EGF-domain (Factor VII has 2 EGF-loops and Protein S has 4 EGF-loops), thus, it will be possible to separate Factor VII and protein contaminants like Protein S due to different affinity for phosphatidylserine, especially in the presence of calcium).

In another embodiment, the solid phase material is hydroxyapatite

In another embodiment of the method defined further above, the solid phase material is a chromatographic material. Examples of suitable solid phase materials are, e.g., those selected from anion exchange materials, cation exchange materials, hydroxyapatite, hydrophobic solid phase materials, etc., cf. the "Experimentals" section.

Various particular aspects of the invention will be described in the following.

Immunoaffinity Using Monoclonal Antibody for Protein Contaminant

According to this aspect of the present invention, at least one of the protein contaminant(s) is bound by a solid phase material carrying monoclonal antibodies. Thus, the composition may simply be contacted with said solid phase material and subsequently separated from the solid phase material so as to obtain an at least less contaminated composition.

Coupling of monoclonal antibodies to a solid phase material can be performed via reactive groups placed on the solid phase material. The most typical used matrices are cyanogen bromide (CNBr) or N-hydroxy-succinimide (NHS) activated supports (Wilchek M. et al., Reactive & Functional Polymers. 1999, 41,263-268). Regarding the CNBr- and NHS activated supports the coupling occurs via primary amino-groups in the antibody leading to an isourea-bond with the CNBr-group and an amide-bond with the NHS-group.

The antibody solution is dissolved or dialysed into a suitable coupling buffer, for instance 0.2 M $NaHCO_3$, 0.5 M NaCl pH 8.3, buffers with primary amino-groups can not be used. The coupling pH depends on the antibody and the activated support but normally pH 6-9 can be used. In order to preserve the stability of the activated support before use it is washed with 10-15 media volumes of ice cold 1 mM HCl. Immediately after the washed support is transferred to the antibody solution and gently mixed and adjusted to the desired pH level. The coupling mixture is left with gentle rotation either a few hours at room temperature or overnight at 4° C. After the coupling is completed, any non-reacted groups on the support are blocked by standing for instance in a Tris, ethanol amine or glycine buffer pH 8-9 for a few hours at room temperature. After blocking the support is washed using a method which alternates high and low pH with for instance the blocking buffer and an acetate buffer pH 3-4.

One particular embodiment relates to a method for reducing the content of one or more protein contaminants in a first composition (such as a cell culture supernatant) comprising a Vitamin K-dependent protein of interest, said method comprising the step of (i) contacting a first (such as an unpurified) composition with a solid phase material carrying monoclonal antibodies raised against at least one of the protein contaminant(s), and (ii) separating the thus resulting second composition from said solid phase material so as to obtain a composition wherein the level of protein contaminant(s) expressed as parts per million relative to the Vitamin K-dependent protein of interest has been reduced by at least a factor of 5.

Thus, it is found to be very beneficial to use a cell culture supernatant directly, i.e. without any preceding purification steps. This may be due to the fact that the protein contaminant(s) may be at least partly cleaved by the Vitamin K-dependent protein of interest if the cell culture supernatant is processed prior to application of the present method whereby a more complex mixture of protein contaminants arises. It may, thus, be even more difficult to reduce the content of protein contaminants when such a complex mixture exists.

This being said, it should be understood that the present invention also provides an alternative method wherein the same steps are applied, but where the liquid composition comprising the Vitamin K-dependent protein of interest is not necessarily a constituent of a cell culture supernatant obtained directly from a cell culture.

The protein contaminant(s) is/are typically host cell proteins, and, thus, the monoclonal antibody is typically raised against a protein contaminant selected from host cell proteins, such as Gla-domain-containing protein contaminants, in particular a protein contaminant selected from GAS-6, Protein S, Factor II (Prothrombin), Factor X/Xa, Factor IX/IXa, Protein C, Factor VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin, more particularly Protein S.

As mentioned hereinabove, the Vitamin K-dependent protein of interest is typically a Vitamin K-dependent coagulation factor selected from Factor VII polypeptides, Factor IX polypeptides, Factor X polypeptides and activated Protein C. In one more particular embodiment, the Vitamin K-dependent protein of interest is a Factor IX polypeptide. In another more particular embodiment, the Vitamin K-dependent protein of interest is a Factor VII polypeptide.

In one embodiment, a predominant amount of protein contaminants are Gla-domain containing polypeptides, in particular Protein S, and the Vitamin K-dependent protein of interest is a Factor VII polypeptide.

This being said, the method renders it possible to yield a level of protein contaminant(s) expressed as parts per million relative to the Vitamin K-dependent protein of interest which has been reduced by at least a factor of 10, or at least a factor of 25, or at least a factor of 50, such as by at least a factor of 100, or at least a factor of 250, or at least a factor of 500, or at least a factor of 750, or at least a factor of 1000, or at least a factor of 2000.

In particular, the total content of protein contaminants in the second (purified) composition is at the most 100 ppm, such as at the most 90 ppm, or at the most 80 ppm, or at the most 70 ppm, or at the most 60 ppm, or at the most 50 ppm, or at the most 40 ppm, or at the most 30 ppm, or at the most 20 ppm, or at the most 10 ppm or at the most 5 ppm; or the total content of Protein S contaminants in the second (purified) composition is at the most 100 ppm, such as at the most 90 ppm, or at the most 80 ppm, or at the most 70 ppm, or at the most 60 ppm, or at the most 50 ppm, or at the most 40 ppm, or at the most 30 ppm, or at the most 20 ppm, or at the most 10 ppm or at the most 5 ppm.

Typical cell culture supernatants may have a significant amount of protein contaminants (in particular Protein S), thus, the total content of protein contaminants in a cell culture supernatant (such as an unpurified cell culture supernatant) is typically at least 500 ppm, such as at least 750 ppm, or at least 1000 ppm, or at least 2000 ppm; or the total content of Protein S contaminants in the unpurified cell culture supernatant is at least 500 ppm, such as at least 750 ppm, or at least 1000 ppm, or at least 2000 ppm.

A particular embodiment of this aspect of the present invention relates to a method for reducing the content of Protein S contaminants in a cell culture supernatant comprising a Factor VII polypeptide, said method comprising the step of (i) contacting a first composition, such as a cell culture supernatant with a solid phase material carrying monoclonal antibodies raised against the Protein S contaminant(s), and (ii) separating the thus resulting second composition from said solid phase material so as to obtain a composition wherein the level of Protein S contaminant(s) expressed as parts per million relative to the Factor VII polypeptide of interest has been reduced by at least a factor of 50.

Immobilised Protein C

According to this aspect of the present invention, at least one of the protein contaminant(s) is bound by a solid phase material carrying immobilised Protein C. Thus, the composition may simply be contacted with said solid phase material and subsequently separated from the solid phase material so as to obtain an at least less contaminated composition.

More particularly, the invention provides a method for reducing the content of protein contaminants in a composition comprising a Vitamin K-dependent protein of interest, said method comprising the step of (i) contacting a first composition with a solid phase material carrying immobilised Protein C, and (ii) separating the thus resulting second composition from said solid phase material so as to obtain a composition wherein the level of protein contaminant(s) expressed as parts per million relative to the Vitamin K-dependent protein of interest has been reduced by at least a factor of 5, such as a method for reducing the content of Protein S in a composition comprising a Factor VII polypeptide, said method comprising the step of (i) contacting a first composition with a solid phase material carrying immobilised Protein C, and (ii) separating the thus resulting second composition from said solid phase material so as to obtain a composition wherein the level of protein contaminant(s) expressed as parts per million relative to the Vitamin K-dependent protein of interest has been reduced by at least a factor of 10.

It should be understood that the above methods for the reduction of the content of protein contaminant(s) may be used alone or in combination, such as in combination. The individual chromatography steps may be carried out in any suitable order. Based on preliminary studies, it is believed that the following combinations provide an excellent overall reduction of the content of protein contaminant(s):

- cation exchange chromatography→immunoaffinity using monoclonal antibodies against protein contaminant→anion exchange chromatography
- cation exchange chromatography→hydrophobic interaction chromatography→anion exchange chromatography
- cation exchange chromatography→hydrophobic interaction chromatography→immunoaffinity using monoclonal antibodies against protein contaminant→anion exchange chromatography
- anion exchange chromatography→immunoaffinity using monoclonal antibodies against protein of interest→immunoaffinity using contaminant monoclonal antibodies→anion exchange chromatography→hydrophobic interaction chromatography
- anion exchange chromatography→hydrophobic interaction chromatography→Cation exchange chromatography
- anion exchange chromatography→hydrophobic interaction chromatography→immunoaffinity using monoclonal antibodies against protein contaminants→Cation exchange chromatography
- anion exchange chromatography→immunoaffinity using monoclonal antibodies against protein of interest→anion exchange chromatography→hydrophobic interaction chromatography
- cation exchange chromatography→hydroxyapatite→anion exchange chromatography
- cation exchange chromatography→hydroxyapatite→immunoaffinity using monoclonal antibodies against protein contaminant→anion exchange chromatography
- immunoaffinity using monoclonal antibodies against protein of interest→hydrophobic interaction chromatography→anion exchange chromatography→immunoaffinity using monoclonal antibodies against protein contaminant→anion exchange chromatography
- immunoaffinity using monoclonal antibodies against protein of interest→anion exchange chromatography→hydrophobic interaction chromatography→immunoaffinity using monoclonal antibodies against protein contaminant→anion exchange chromatography
- hydroxyapatite→hydrophobic interaction chromatography→cation exchange chromatography→anion exchange chromatography
- hydroxyapatite→immunoaffinity using monoclonal antibodies against protein contaminant→cation exchange chromatography→anion exchange chromatography
- immunoaffinity using monoclonal antibodies against protein contaminant→hydrophobic interaction chromatography→anion exchange chromatography
- immunoaffinity using monoclonal antibodies against protein contaminant→hydrophobic interaction chromatography→gelfiltration→anion exchange chromatography
- immunoaffinity using monoclonal antibodies against protein contaminant→cation exchange chromatography→hydrophobic interaction chromatography→anion exchange chromatography
- immunoaffinity using monoclonal antibodies against protein of interest→anion exchange chromatography→hydrophobic interaction chromatography→cation exchange chromatography In a particular embodiment, immunoaffinity using monoclonal antibodies against protein of interest is used as the first step of the purification process. Thus, it is found to be very beneficial to use a cell culture supernatant directly, i.e. without any preceding purification steps. It should be understood that reduction of the protein contaminant(s) typically is by at least a factor of 2, such as by at least a factor of 5, in each of the steps of the multi-step methods described above.

Novel Compositions Comprising a Vitamin K-Dependent Protein of Interest

It is believed that the methods of the present invention give rise to compositions of Vitamin K-dependent proteins, in particular Factor VII polypeptides, which in themselves are novel.

Hence, a further aspect of the present invention relates to a composition comprising a Vitamin K-dependent protein of interest produced under cell culture conditions, wherein the total content of protein contaminants is at the most 100 ppm based on the content of the Vitamin K-dependent protein of interest. In most embodiments hereof, the content of the protein contaminants is in the range of 0.01-100 ppm, such as 0.01-50 ppm, e.g. 0.05-25 ppm, or 0.05-20 ppm, or 0.05-15 ppm, or 0.05-10 ppm, or 0.05-5 ppm.

An alternative aspect of the present invention relates to a composition comprising a Factor VII polypeptide obtained from a serum-free, non-human cell culture, wherein the total content of Protein S contaminants is at the most 100 ppm based on the content of the Factor VII polypeptide. In most embodiments hereof, the content of the protein contaminants is in the range of 0.01-100 ppm, such as 0.01-50 ppm, e.g. 0.05-25 ppm, or 0.05-20 ppm, or 0.05-15 ppm, or 0.05-10 ppm, or 0.05-5 ppm.

In the above aspects, the Vitamin K-dependent protein of interest is typically a Vitamin K-dependent coagulation factor selected from Factor VII polypeptides, Factor IX polypeptides, Factor X polypeptides and activated Protein C. In one more particular embodiment, the Vitamin K-dependent protein of interest is a Factor IX polypeptide. In another more particular embodiment, the Vitamin K-dependent protein of interest is a Factor VII polypeptide.

A more particular embodiment of the above relates to a composition comprising a Factor VII polypeptide produced under cell culture conditions, wherein the total content of Protein S contaminants is at the most 100 ppm based on the content of the Factor VII polypeptide.

The present invention is further illustrated by the following embodiments:

1. A method for reducing the content of one or more protein contaminants in a composition comprising a Vitamin K-dependent protein of interest, said method comprising at least the steps of (i) contacting a first composition with a solid phase material which is able to bind the one or more protein contaminants and/or the Vitamin K-dependent protein of interest, and (ii) collecting a resulting second composition comprising the Vitamin K-dependent protein of interest, whereby the level of protein contaminant(s) expressed as parts per million relative to the Vitamin K-dependent protein of interest has been reduced from said first composition to said resulting second composition by at least a factor of 2, such as at least 5, such as at least 10, such as at least 20, such as at least 50, such as at least 100.

2. The method according to embodiment 1, wherein the total content of protein contaminants in the resulting second composition comprising the Vitamin K-dependent protein of interest is at the most 100 ppm.

3. The method according to any one of the embodiments 1-2, wherein the Vitamin K-dependent protein of interest is a Vitamin K-dependent coagulation factor selected from Factor VII polypeptides, Factor IX polypeptides, Factor X polypeptides and activated Protein C.

4. The method according to embodiment 1-3, wherein the Vitamin K-dependent protein of interest is a Factor IX polypeptide.

5. The method according to embodiment 1-3, wherein the Vitamin K-dependent protein of interest is a Factor VII polypeptide, such as wild type human Factor VIIa.

6. The method according to embodiment 5, wherein the Factor VII polypeptide comprises an amino acid substitution selected from P10Q and K32E.

7. The method according to any one of the embodiments 1-6, wherein the predominant amount of protein contaminants are Gla-domain containing polypeptides, in particular Protein S, and wherein the Vitamin K-dependent protein of interest a Factor VII polypeptide.

8. The method according to any one of the embodiments 1-7, wherein the level of protein contaminant(s) expressed as parts per million relative to the Vitamin K-dependent protein of interest has been reduced by at least a factor of 10, or at least a factor of 25, or at least a factor of 50, such as by at least a factor of 100, or at least a factor of 250, or at least a factor of 500, or at least a factor of 750, or at least a factor of 1000, or at least a factor of 2000, or at least a factor of 5000.

9. The method according to any one of the embodiments 1-8, wherein the total content of protein contaminants in the resulting second composition comprising the Vitamin K-dependent protein of interest is at the most 100 ppm, such as at the most 50 ppm, such as at the most 10 ppm, such as at the most 5 ppm, such as at the most 2 ppm, such as at the most 1 ppm.

10. The method according to any one of the embodiments 1-9, wherein the total content of protein contaminants in the first composition is at least 500 ppm.

11. The method according to any one of the embodiments 1-10, wherein the total content of Protein S contaminants in the first composition is at least 500 ppm.

12. A method for reducing the content of one or more Protein S contaminants in a composition comprising a Factor VII polypeptide, said method comprising at least the steps of (i) contacting a first composition with a solid phase material which is able to bind the Protein S contaminant(s) and/or the Factor VII polypeptide, and (ii) collecting a resulting second composition comprising the Factor VII polypeptide, whereby the level of Protein S contaminant(s) expressed as parts per million relative to the Factor VII polypeptide has been reduced by at least a factor of 2, such as 5.

13. The method according to any one of the embodiments 1-11 and 12, wherein the solid phase material binds a relatively higher amount of the protein contaminant compared to the Vitamin K-dependent protein of interest.

14. The method according to embodiment 13, wherein the solid phase material specifically binds at least one of the contaminants, e.g. by strong affinity or by covalent binding of said contaminant(s), such as by formation of disulphide bonds to thiol moieties of said contaminant(s).

15. The method according to any one of embodiments 13 and 14, wherein the solid phase material is carrying monoclonal antibodies raised against at least one of the protein contaminant(s).

16. The method according to embodiment 15, wherein the composition comprising the Vitamin K-dependent protein of interest is a constituent of a cell culture supernatant.

17. The method according to embodiment 14, wherein the solid phase material is carrying immobilised Protein C.

18. The method according to any one of the embodiments 1-11 and 12, wherein the solid phase material binds a relatively higher amount of the Vitamin K-dependent protein of interest compared to the protein contaminant(s).

19. The method according to embodiment 18, wherein the solid phase material specifically binds the Vitamin K-dependent protein of interest.

20. The method according to any one of embodiments 18 and 19, wherein the solid phase material is carrying monoclonal antibodies raised against the Vitamin K-dependent protein of interest or an analogue thereof.

21. The method according to any one of embodiments 18 and 19, wherein the solid phase material is a triazin ligand with affinity for the Vitamin K-dependent protein of interest or an analogue thereof.

22. The method according to any one of embodiments 18 and 19, wherein the solid phase material is carrying an inhibitor for said Vitamin K-dependent protein of interest, or is carrying a metal which is capable of chelating with said Vitamin K-dependent protein of interest, or is carrying immobilized tissue factor (thromboplastin), or is carrying immobilized heparin.

23. The method according to embodiment 22, wherein the inhibitor for said Vitamin K-dependent protein of interest is a benzamidine- or a guanidine-type inhibitor such as those comprising a —C(=N—Z$^1$—R$^1$)—NH—Z$^2$—R$^2$ motif, wherein Z$^1$ and Z$^2$ independently are selected from the group consisting of —O—, —S—, —NRH— and a single bond, where R$^H$ is selected from the group consisting of hydrogen, C$_{1-4}$-alkyl, aryl and arylmethyl, and R$^1$ and R$^2$ independently are selected from the group consisting of hydrogen, optionally substituted C$_{1-6}$-alkyl, optionally substituted C$_{2-6}$-alkenyl, optionally substituted aryl, optionally substituted heterocyclyl, or Z$^2$ and R$^2$ are as defined above and —C=N—Z$^1$—R$^1$ forms part of a heterocyclic ring, or Z$^1$ and R$^1$ are as defined above and —C—NH—Z$^2$—R$^2$ forms part of a heterocyclic ring, or —C(=N—Z$^1$—R$^1$)—NH—Z$^2$—R$^2$ forms a heterocyclic ring wherein —Z$^1$—R$^1$—R$^2$—Z$^2$— is a biradical.

24. The method according to any one of embodiments 1-11 and 12, wherein the solid phase material is a chromatographic material.

25. The method according to any one of embodiments 1-11 and 12, wherein the solid phase material is bound to a membrane.

26. The method according to embodiment 22-23, wherein the solid phase material is an anion exchange material.

27. The method according to embodiment 26, wherein elution from anion exchange is performed by increasing the concentration of a calcium salt such as CaCl$_2$.

28. The method according to embodiment 26, wherein elution from anion exchange is performed by increasing the concentration of a magnesium salt such as MgCl$_2$.

29. The method according to embodiment 24, wherein the solid phase material is a cation exchange material.

30. The method according to embodiment 24, wherein the solid phase material is hydroxyapatite.

31. The method according to embodiment 24, wherein the solid phase material is a hydrophobic solid phase material.

32. A method for reducing the content of one or more protein contaminants in a composition (in particular a cell culture supernatant) comprising a Vitamin K-dependent protein of interest, said method comprising the step of (i) contacting a first composition with a solid phase material carrying monoclonal antibodies raised against at least one of the protein contaminant(s), and (ii) separating the resulting second composition from said solid phase material so as to obtain a composition wherein the level of protein contaminant(s) expressed as parts per million relative to the Vitamin K-dependent protein of interest has been reduced by at least a factor of 5.

33. The method according to embodiment 32, wherein the monoclonal antibody is raised against a protein contaminant selected from host cell proteins, such as Gla-domain-containing protein contaminants, in particular a protein contaminant selected from GAS-6, Protein S. Factor II (Prothrombin), thrombin, Factor X/Xa, Factor IX/IXa, Protein C, Factor VII/VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin, more particularly Protein S.

34. The method according to any one of the embodiments 27-28, wherein the Vitamin K-dependent protein of interest is a Vitamin K-dependent coagulation factor selected from Factor VII polypeptides, Factor IX polypeptides, Factor X polypeptides and activated Protein C.

35. The method according to embodiment 29, wherein the Vitamin K-dependent protein of interest is a Factor IX polypeptide.

36. The method according to embodiment 29, wherein the Vitamin K-dependent protein of interest is a Factor VII polypeptide.

37. The method according to any one of the embodiments 32-36, wherein the predominant amount of protein contaminants are Gla-domain containing polypeptides, in particular Protein S, and wherein the Vitamin K-dependent protein of interest is a Factor VII polypeptide.

38. The method according to any one of the embodiments 32-37, wherein the predominant amount of protein contaminants is hamster Protein S.

39. The method according to any one of the embodiments 32-38, wherein the level of protein contaminant(s) expressed as parts per million relative to the Vitamin K-dependent protein of interest has been reduced by at least a factor of 10, or at least a factor of 25, or at least a factor of 50, such as by at least a factor of 100, or at least a factor of 250, or at least a factor of 500, or at least a factor of 750, or at least a factor of 1000, or at least a factor of 2000.

40. The method according to any one of the embodiments 32-39, wherein the total content of protein contaminants in the resulting second composition is at the most 100 ppm.

41. The method according to any one of the embodiments 32-40, wherein the total content of Protein S contaminants in the resulting second composition is at the most 100 ppm.

42. The method according to any one of the embodiments 32-41, wherein the total content of protein contaminants in the first composition is at least 500 ppm.

43. The method according to any one of the embodiments 32-42, wherein the total content of Protein S contaminants in the first composition is at least 500 ppm.

44. A method for reducing the content of Protein S contaminants in a composition, such as in a cell culture supernatant, comprising a Factor VII polypeptide, said method comprising the step of (i) contacting a first composition, such as a cell culture supernatant with a solid phase material carrying monoclonal antibodies raised against the Protein S contaminant(s), and (ii) separating a resulting second composition from said solid phase material so as to obtain a composition wherein the level of Protein S contaminant(s) expressed as parts per million relative to the Factor VII polypeptide of interest has been reduced by at least a factor of 50.

45. A method for reducing the content of protein contaminants in a composition comprising a Vitamin K-dependent protein of interest, said method comprising the step of (i) contacting a first composition with a solid phase material carrying immobilised Protein C, and (ii) separating a resulting second composition from said solid phase material so as to obtain a composition wherein the level of protein contaminant(s) expressed as parts per million relative to the Vitamin K-dependent protein of interest has been reduced by at least a factor of 5.

46. The method according to embodiments 45 wherein the Vitamin K-dependent protein of interest is a Vitamin K-dependent coagulation factor selected from Factor VII polypeptides, Factor IX polypeptides, Factor X polypeptides and activated Protein C.

47. The method according to embodiment 46, wherein the Vitamin K-dependent protein of interest is a Factor IX polypeptide.

48. The method according to embodiment 46, wherein the Vitamin K-dependent protein of interest is a Factor VII polypeptide.

49. The method according to any one of the embodiments 45-48, wherein the predominant amount of protein contaminants are Gla-domain containing polypeptides, in particular Protein S, and wherein the Vitamin K-dependent protein of interest is a Factor VII polypeptide.

50. The method according to any one of the embodiments 45-49, wherein the level of protein contaminant(s) expressed as parts per million relative to the Vitamin K-dependent protein of interest has been reduced by at least a factor of 10, or at least a factor of 25, or at least a factor of 50, such as by at least a factor of 100, or at least a factor of 250, or at least a factor of 500, or at least a factor of 750, or at least a factor of 1000, or at least a factor of 2000.

51. The method according to any one of the embodiments 45-50, wherein the total content of protein contaminants in said resulting second composition is at the most 100 ppm.

52. The method according to any one of the embodiments 45-51, wherein the total content of Protein S contaminants in said resulting second composition is at the most 100 ppm.

53. The method according to any one of the embodiments 45-52, wherein the total content of protein contaminants in said first composition is at least 500 ppm.

54. The method according to any one of the embodiments 45-53, wherein the total content of Protein S contaminants in said first composition is at least 500 ppm.

55. A method for reducing the content of Protein S in a composition comprising a Factor VII polypeptide, said method comprising the step of (i) contacting a first composition with a solid phase material carrying immobilised Protein C, and (ii) separating the resulting second composition from said solid phase material so as to obtain a composition wherein the level of protein contaminant(s) expressed as parts per million relative to the Vitamin K-dependent protein of interest has been reduced by at least a factor of 10.

56. A method for reducing the content of one or more protein contaminants in a cell culture supernatant comprising a Vitamin K-dependent protein of interest, said method comprising the step of (i) contacting the cell culture supernatant with a solid phase material carrying monoclonal antibodies raised against the Vitamin K-dependent protein of interest or an analogue thereof, (ii) optionally washing said solid phase material, and (iii) eluting the Vitamin K-dependent protein of interest from said solid phase material so as to obtain a resulting composition wherein the level of protein contaminant(s) expressed as parts per million relative to the Vitamin K-dependent protein of interest has been reduced by at least a factor of 5.

57. The method according to embodiment 56, wherein the Vitamin K-dependent protein of interest is a Vitamin K-dependent coagulation factor selected from Factor VII polypeptides, Factor IX polypeptides, Factor X polypeptides and activated Protein C.

58. The method according to embodiment 57, wherein the Vitamin K-dependent protein of interest is a Factor IX polypeptide.

59. The method according to embodiment 57, wherein the Vitamin K-dependent protein of interest is a Factor VII polypeptide.

60. The method according to any one of the embodiments 56-59, wherein the predominant amount of protein contaminants are Gla-domain containing polypeptides, in particular Protein S, and wherein the Vitamin K-dependent protein of interest is a Factor VII polypeptide.

61. The method according to any one of the embodiments 56-60, wherein the level of protein contaminant(s) expressed as parts per million relative to the Vitamin K-dependent protein of interest has been reduced by at least a factor of 10, or at least a factor of 25, or at least a factor of 50, such as by at least a factor of 100, or at least a factor of 250, or at least a factor of 500, or at least a factor of 750, or at least a factor of 1000, or at least a factor of 2000.

62. The method according to any one of the embodiments 56-61, wherein the total content of protein contaminants in said resulting composition is at the most 100 ppm.

63. The method according to any one of the embodiments 56-62, wherein the total content of Protein S contaminants in said resulting composition is at the most 100 ppm.

64. The method according to any one of the embodiments 56-63, wherein the total content of protein contaminants in the cell culture supernatant is at least 500 ppm.

65. The method according to any one of the embodiments 56-64, wherein the total content of Protein S contaminants in the cell culture supernatant is at least 500 ppm.

66. A method for reducing the content of protein contaminants in a cell culture supernatant comprising a Factor VII polypeptide, said method comprising the step of (i) contacting the cell culture supernatant with a solid phase material carrying monoclonal antibodies raised against the Factor VII polypeptide or an analogue thereof, (ii) optionally washing said solid phase material, and (iii) eluting the Factor VII polypeptide from said solid phase material so as to obtain a resulting composition wherein the level of protein contaminants expressed as parts per million relative to the Factor VII polypeptide has been reduced by at least a factor of 100.

67. A method for reducing the content of Protein S in a cell culture supernatant comprising a Factor VII polypeptide, said method comprising the step of (i) contacting the cell culture supernatant with a solid phase material carrying monoclonal antibodies raised against the Factor VII polypeptide or an analogue thereof, (ii) optionally washing said solid phase material, and (iii) eluting the Factor VII polypeptide from said solid phase material so as to obtain a resulting composition wherein the level of protein S expressed as parts per million relative to the Factor VII polypeptide has been reduced by at least a factor of 100.

68. A composition comprising a Vitamin K-dependent protein of interest produced under cell culture conditions, wherein the total content of protein contaminants is at the most 100 ppm based on the content of the Vitamin K-dependent protein of interest.

69. The composition according to embodiment 68, wherein the content of the protein contaminants is in the range of 0.01-100 ppm, such as 0.01-50 ppm, e.g. 0.05-25 ppm, or 0.05-20 ppm, or 0.05-15 ppm, or 0.05-10 ppm, or 0.05-5 ppm.

70. A composition comprising a Factor VII polypeptide obtained from a serum-free, non-human cell culture, wherein the total content of Protein S contaminants is at the most 100 ppm based on the content of the Factor VII polypeptide.

71. A composition comprising a Factor IX polypeptide, obtained from a serum-free, non-human cell culture, wherein the total content of Protein S contaminants is at the most 100 ppm based on the content of the Factor IX polypeptide.

72. The composition according to any one of the embodiments 67-71, wherein the content of the Protein S contaminants is in the range of 0.01-100 ppm, such as 0.01-50 ppm, e.g. 0.05-25 ppm, or 0.05-20 ppm, or 0.05-15 ppm, or 0.05-10 ppm, or 0.05-5 ppm.

73. The composition according to any one of the embodiments 67-72, wherein the Vitamin K-dependent protein of interest is a Vitamin K-dependent coagulation factor selected from Factor VII polypeptides, Factor IX polypeptides, Factor X polypeptides and activated Protein C.

74. The composition according to embodiment 73, wherein the Vitamin K-dependent protein of interest is a Factor IX polypeptide.

75. The composition according to embodiment 73, wherein the Vitamin K-dependent protein of interest is a Factor VII polypeptide.

76. A composition comprising a Factor VII polypeptide produced under cell culture conditions, wherein the total content of Protein S contaminants is at the most 100 ppm, such as in the range of 0.01-100 ppm, based on the content of the Factor VII polypeptide.

EXPERIMENTALS

Monoclonal Anti Hamster Protein S Antibodies

These antibodies have been developed using RBF mice immunised with a hamster Protein S pool isolated from SF-Factor VIIa production, and by using a fusion technique involving FoxNy myelomas as fusion partner to the RBF splenocytes. The said monoclonal antibodies recognize any epitope outside the thrombin cleavage site as well as outside the C4BP binding area. Furthermore the said monoclonal antibodies can be $Ca^{2+}$ independent as well as $Ca^{2+}$ dependent. The said monoclonal antibody can be of any Ig class.

The $Ca^{2+}$ independent monoclonal anti hamster protein S antibodies are intended to be used for the detection of hamster Protein S contamination in any drug produced from CHO cells. Furthermore, it is the intention to use the $Ca^{2+}$ dependent monoclonal anti hamster Protein S antibodies for isolation and purification of hamster Protein S from the production of drugs produced by CHO cells, and in particular to reduce (such as eliminate) the content Protein S in Vitamin K-dependent protein compositions.

RBF mice were immunised with hamster Protein S isolated from the SF-Factor VIIa production (batch HW3-029 pool, contains <1% Factor VIIa). After 6 weeks two fusions were performed using FoxNy myelomas. Several hybridomas were isolated and tested for their binding capacity to Protein S under varying concentrations of $Ca^{2+}$, ranging from no $Ca^{2+}$ present to a $Ca^{2+}$ concentration of 35 mM $Ca^{2+}$. Four monoclonals (ProS-1 F18, ProS-1 F22, ProS-2 F32 and ProS-2 F46) were chosen for their $Ca^{2+}$ independence and isotyped to be either of the IgG1 or the IgG2a isotype. A Sandwich ELISA assay was developed using two (ProS-1 F18 and ProS-2 F32) of the four $Ca^{2+}$ independent antibodies for determination of hamster Protein S contamination in $Ca^{2+}$ dependency as these two antibodies showed good cooperation. The relative affinity of the four $Ca^{2+}$ independent monoclonal antibodies was quite low. Furthermore, we have shown that there is not cross-reactivity to Factor VIIa. One monoclonal, ProS-1 F22, was used in an ELISA for human Protein S detection. F22 did not recognize human Protein S at all. Most likely this is the case for the monoclonals as well. Furthermore we have developed three $Ca^{2+}$ dependent antibodies, ProS-2 F15, ProS-2 F35 and ProS-2 F44, neither of which binds to any Protein S in the presence of 20 mM Citrate, i.e. when there is no $Ca^{2+}$ present. The binding capacity of the three antibodies to Protein S varies with the concentration of $Ca^{2+}$ (ranging form 2.5 mM to 35 mM $Ca^{2+}$), but are all significantly different from when there is no $Ca^{2+}$ present. The three antibodies has been frozen until further notice.

Determination of Content of Hamster Protein S, ELISA Using Monoclonal Antibodies The relative content of hamster Protein S is determined with a sandwich ELISA using two different monoclonal antibodies. The antibodies were developed in mice using purified protein S from CHO cells.

A 96 well Nunc maxisorb microtiterplate is coated with the antibody ProS-2-F32 the antibody's function is to capture the antigen.

The coating procedure is as follows: 100 µl of a solution containing approximately 5 µg/ml ProS-2-F32 (stock solution with 1.93 mg/ml is diluted 1:386 in 0.1 M $Na_2HCO_3$ pH 9.8) is applied to each well in the 96 well Nunc microtiteplate, a plate sealer is added on top of the plate and the plate is incubated over night between 1 and 9° C.

Day 2, After the primary incubation the solution is discarded and each of the wells are blocked as follows: Add 350 µl blocking buffer (Phosphate buffer with saline (PBS), 0.010 M phosphate and 0.15 M NaCl, 0.1% Tween 20 pH 7.2) to each well, and a plate sealer to the plate and incubate the plate for 1 hr at room temperature, where room temperature is defined as being between 18 and 25° C. After the blocking-incubation time is completed, discard the solution and wash each well three independent times using 350 µl of a washing buffer (0.010 M phosphate and 0.15 M NaCl, 0.05% Tween 20 pH 7.2).

The calibrators and samples are appropriately diluted in a citrate containing Tris buffer (0.010 M Tris; 0.15 M NaCl, 0.050 M Citrat, 0.1% v/v Tween 20, pH 8.6.), controls are diluted in Tris buffer with carrier protein (0.010 M Tris, 0.15 M NaCl, 0.1% v/v Tween 20, 1% BSA, pH 8.0.). 100 µl of each of the calibrators, controls and samples are applied to the Nunc plate, a plate sealer is added and the plate is incubated O/N between 1 and 9° C.

Day 3. The wells are emptied and the plate washed 3 times, as above using the PBS washing buffer and the biotin labelled antibody ProS-1-F18 is added for detection of the antigen-antibody complex. The biotin labelled ProS-1-F18 antibody solution is diluted 1:1000 in TBS, (0.010 M Tris; 0.15 M NaCl, 0.1% Tween 20 pH 8.6) and 100 µl is added to each well, the plate sealer is applied and the plate is incubated for 1 hr at R/T. Discard the solution and wash the plate 3 times, as above using 350 µl of the PBS washing buffer.

Apply 100 µl of a Horseradish Peroxidase avidin D solution, diluted 1:10000 in a TBS (0.010 M Tris; 0.15 M NaCl, 0.1% Tween 20 pH 8.6), apply the plate sealer and incubate the plate for 1 hour at room temperature. Wash the plate 3 times with PBS, washing buffer and finally add 100 µl TMB substrate. Incubate the plate 10 minutes at room temperature in the dark, add 100 µl 2 M phosphoric acid to stop the reaction and measure the absorbance at 450 nm using 620 nm as reference.

Determination of Content of Hamster Protein S, ELISA Using Polyclonal Antibodies:

The content of hamster Protein S was determined in a sandwich ELISA based on polyclonal antibodies.

Coating with primary antibodies: A 96 well Nunc maxisorb microplate was coated with the polyclonal antibody Rb-α-Hu Protein S (Dakocytomation code nr. A0384). The antibody solution, which had a protein concentration of 4.1 mg/ml, was diluted in coating buffer (Bicarbonate buffer, pH 9.6; 3.03 g Na2CO3; 5.98 g $NaHCO_3$; Water to 1 l) to 5.0 µg/ml (corresponding to a 1:820 dilution). 100 µl were added to each well, except wells A1 and A2, which were used as blanks. The plate was incubated overnight at 4° C.

The following morning, the solution was discarded and the plate was washed 3 times (350 µl) with washing buffer (Tween/PBS). The plate (except wells A1 and A2) was subsequently blocked using the dilution buffer (BSA/Tween/PBS). The plate was left to block at room temperature for 1 hour with a plate sealer, before it was washed 3 times (350 μl) with washing-buffer (Washing buffer (PBS/Tween, pH 7.4); 16.0 g NaCl; 0.40 g KH2PO4; 2.30 g Na2HPO4; 0.40 g KCl; 1 ml tween 20; Water to 2 l).

Samples, Controls and standards: A protein S standard with a concentration of 1120 μg/ml was diluted in dilution buffer (Dilution buffer (BSA/Tween/PBS):0.5 g bovine serum albumin (Sigma, A-7030); Washing buffer to 100 ml) to a concentration of 25 ng/ml (1:44800). This standard was further diluted in dilution buffer by 2-fold steps to the lowest standard of 0.78 ng/ml. The positive control consists of human protein S (American Diagnostica, code 443) which was diluted in dilution buffer to a concentration of 2.5 ng/ml. A conjugate control was added by adding just dilution buffer to a pair of wells. The samples were diluted in dilution buffer, aiming at a concentration between 1 and 10 ng/ml, which corresponds to the linear section of the standard curve. All standards, controls and samples were put on the plate as duplicates and incubated overnight with a plate sealer at 4° C.

Incubation with HRP conjugated Secondary antibodies: The wells were emptied and the plate washed 3 times, as above using the Tween/PBS washing buffer. Rb-α-human Protein S, HRP (Dakocytomation code nr. P0419) was diluted 1000 fold in dilution buffer and 100 μl was added to each well except A1+A2. The plate was left to incubate an a shaker for one hour at room temperature before it was washed 3 times (350 μl) with washing-buffer.

Detection: 100 μl of substrate solution was added to all wells. The substrate solution consisted of 4 OPD tablets, 2 mg each, (Dakocytomation code S2045) in 12 ml of ultra pure water and 5 μl 30% $H_2O_2$ immediately before use. The reaction was allowed to run for 15 min before it was stopped by adding 50 μl of 2.5 M $H_2SO_4$ per well. The plate was read in a microplate reader at 492 nm.

A. Immunoaffinity Using Anti-Protein S Monoclonal Antibodies

Example 1

Reduction of Protein S is performed on an Amersham HiTrap NHS activated column (1 ml column volume (CV)) coupled with monoclonal antibodies (MAb) raised in mice against hamster Protein S (0.4 mg MAb per ml packed column). The column is equilibrated with 10 CV 10 mM $Na_2HPO_4$, 150 mM NaCl pH 7.5 and the load is 100 CV of a solution with a conductivity of 14 mS/cm containing 1.49 mg/ml Factor VIIa and a content of Protein S of more than 300 ppm (calcium is chelated with citrate) followed by a wash of 10 CV 10 mM $Na_2HPO_4$, 150 mM NaCl pH 7.5. The entire step is operated at a flow rate of 60 CV/h and a temperature of 5° C. Small traces of Protein S and Factor VIIa is eluted with 20 mM $Na_2HPO_4$, 2 M NaCl pH 7.2 (confirmed by SDS-PAGE/silverstain), subsequently the bound Protein S is eluted with 50 mM citrate pH 3.0 and a small fraction of Factor VIIa (<1% of the amount from the load) is desorbed with 50 mM glycin pH 2.0. The column is re-equilibrated with 10 CV of $Na_2HPO_4$, 150 mM NaCl pH 7.5. A Protein S level below 30 ppm, i.e. a reduction by a factor of at least 10 is measured by ELISA in the run-through.

Example 2

Reduction of Protein S is performed on an Amersham HiTrap NHS activated column (1 ml column volume (CV)) coupled with monoclonal antibodies (MAb) raised in mice against hamster Protein S (0.4 mg MAb per ml packed column). The column is equilibrated with 10 CV 15 mM Tris, 150 mM NaCl pH 7.5 and the load is 108 CV of a solution with a conductivity of 12 mS/cm containing a content of Protein S of more than 150 ppm (10 mM calcium present) followed by a wash of 10 CV 15 mM Tris, 150 mM NaCl pH 7.5. The load and wash is run at a flow rate of 24 CV/h, the rest of the program at 60 CV/hr, and a temperature of 5° C. The column is cleaned with 15 CV 50 mM citrate pH 3.0 then re-equilibrated with 10 CV 15 mM Tris, 150 mM NaCl pH 7.5 and finally cleaned with 12 CV 50 mM glycin pH 2.0 and re-equilibrated with 10 CV of 15 mM Tris, 150 mM NaCl pH 7.5 A Protein S level below 15 ppm, i.e. a reduction by a factor of at least 10 is measured by ELISA in the run-through.

Example 3

Reduction of Protein S was performed on a CNBr-activated Sepharose 4 FF media from GE Healthcare immobilised with a monoclonal antibody (MAb) raised in mice against hamster Protein S (0.8 mg Protein S MAb per ml media). The column (1 ml) was equilibrated with 10 CV 75 mM Tris, 30 mM tri-Na-citrate pH 7.5 and the load was 32 CV of a solution with a Protein S content of 665 ng/ml≈485 ng/mg rFVIIa followed by a 20 CV wash with 75 mM Tris, 30 mM tri-Na-citrate pH 7.5. The column was regenerated with 10 CV 50 mM glycine pH 2.0 and re-equilibrated with 8 CV of 75 mM Tris, 30 mM tri-Na-citrate pH 7.5. A Protein S level of 2.6 ng/ml≈3 ng/mg rFVIIa, i.e. a reduction by a factor of at least 160, was measured by ELISA in the run-through fraction. The load and wash was performed at a flow rate of 7.2 CV/h, the rest of the program at 40 CV/h. The temperature was 5° C.

Example 4

As an alternative to a packed bed column reduction of Protein S was performed on a Sartorius epoxy-activated membrane unit (membrane volume=2.1 ml) immobilised with a monoclonal antibody (MAb) raised in mice against hamster Protein S (1 mg Protein S MAb per membrane unit). The membrane was equilibrated with 10 MV (membrane volume) 75 mM Tris, 30 mM tri-Na-citrate pH 7.5 and the load was 14 MV of a solution with a Protein S content of 683 ng/ml≈502 ng/mg rFVIIa followed by a 8 MV wash with 75 mM Tris, 30 mM tri-Na-citrate pH 7.5. The membrane was regenerated with 10 MV 50 mM glycine pH 2.0 and re-equilibrated with 8 MV of 75 mM Tris, 30 mM tri-Na-citrate pH 7.5. A Protein S level of 9.1 ng/ml≈8 ng/mg rFVIIa, i.e. a reduction by a factor of at least 62, was measured by ELISA in the run-through fraction. The membrane process was performed at a flow rate of 143 MV/h and a temperature of 5° C.

Example 5

Purification of a FIX Solution

Reduction of Protein S is performed on an Amersham NHS activated Sepharose FF column (0.9 ml column volume (CV)) coupled with monoclonal antibodies (MAb) raised in mice against hamster Protein S (0.8 mg MAb per ml packed column). The column is equilibrated with 10 CV 15 mM Tris, 150 mM NaCl, pH 7.5. BeneFIX (1000 IE; Batch no. LE 07D002AF) was suspended in 10 mL of water as described by the package leaflet. 5 mL of this solution containing approximately 2 mg of FIX was loaded onto the column. The content of Protein S was measured by monoclonal ELISA to 230 ng/mL, about 1150 ng protein S in total. The column was washed with 10 CV of equilibration buffer and eluted with 15 mM Tris, 2 M NaCl, pH 7.5. FIX was found in washing and elution fractions. The content of Protein S was measured by monoclonal ELISA to 26 and 52 ng in the washing and elution fractions, respectively.

B. Anion Exchange Chromatography

Example 6

Performing Anion Exchange Chromatography at pH 8.6

Anion exchange chromatography was performed on a column (1 cm in inner diameter×1.3 cm length=1.0 ml column volume (CV)) packed with Amersham Q-Sepharose FF, equilibrated with 5 CV 10 mM glycylglycin, 175 mM NaCl, 8.6. The load was 35 ml of a solution containing a content of Protein S of more than 300 ppm. The column was washed with 7 CV 10 mM glycylglycin, 175 mM NaCl and 4 CV 10 mM glycylglycin, 50 mM NaCl. Elution was performed using a 20 CV linear gradient from 0 mM $CaCl_2$ to 15 mM $CaCl_2$, buffered with glycylglycine containing 50 mM NaCl. The purification was performed at a flowrate of 40 CV/h and at a temperature of 5° C. The pool contained a Protein S level below 30 ppm, i.e. a reduction by a factor of at least 10.

Example 7

Performing Anion Exchange Chromatography at pH 8.6 for Purification of a Fix-Solution Using NaCl Elution Anion exchange chromatography was performed on a column (0.5 cm in inner diameter×5 cm length=1.0 ml column volume (CV)) packed with Amersham Q-Sepharose FF, equilibrated with 10 CV 10 mM Tris, 175 mM NaCl, 8.6. BeneFIX (1000 IE; Batch no. LE 07D051AD) was suspended in 10 mL of water as described by the package leaflet. 3 mL of this solution containing approximately 1.2 mg of FIX was loaded onto the column. The content of Protein S was measured by polyclonal ELISA to 280 ng/mL, a total of 840 ng in the loading solution. The column was washed with 7 CV of equilibration buffer followed by washing with 3 CV of 15 mM Tris, 50 mM NaCl, pH 8.6. The column was subsequently washed with this washing buffer while increasing the amount of $CaCl_2$ (3-5-7-9 mM) over isocratic steps of 5 CV followed by 10 CV of 15 mM Tris, 50 mM NaCl, 15 mM $CaCl_2$. Elution of FIX was performed by 10 mM Tris, 1 M NaCl. SDS-PAGE showed a weak band in the last washing fraction with the buffer containing 15 mM $CaCl_2$.

The amount of Protein S in the elution fraction was measured by polyclonal ELISA to be less than 1.5 ng/mL or less than 7.5 ng.

Example 8

Performing Anion Exchange Chromatography at pH 8.0 for Purification of a FVII-Polypeptide Comprising Amino Acid Substitutions P10Q and K32E Anion exchange chromatography was performed on a column (1 cm in inner diameter×3.2 cm length=2.5 ml column volume (CV)) packed with Amersham Q-Sepharose FF, equilibrated with 10 CV 10 mM Tris, 50 mM NaCl, pH 8. 150 mL culture supernatant containing the FVII variant with P10Q, K32E mutations was added 2.2 mL of a 0.5 M EDTA solution. The conductivity was adjusted by addition of 260 mL WFI (water for injection). The content of Protein S was measured by ELISA to 284 ng/mL or 97 microgram in total. The column was washed with 10 CV of 10 mM Tris, 175 mM NaCl, pH 8 followed by washing with equilibration buffer. The elution was performed by 10 mM Tris, 50 mM NaCl, 35 mM $CaCl_2$, pH 8. The content of Protein S was measured by polyclonal ELISA to 18 µg in the elution pool. The purification was performed at a flow rate of 24 CV/h and at room temperature.

Example 9

Performing Anion Exchange Chromatography at pH 6.0 Using a $MgCl_2$ Gradient Elution Anion exchange chromatography was performed on a column (1 cm in inner diameter×3.2 cm length=2.5 ml column volume (CV)) packed with Amersham Q-Sepharose FF, equilibrated with 10 CV 10 mM histidine, 175 mM NaCl, pH 6. 8 mL of a solution containing 1.6 mg/mL of FVII polypeptide was loaded onto the column. The content of Protein S was measured by ELISA to 360 ng/mL or 2900 ng in total. The column was washed with 10 CV of equilibration buffer followed by washing with 5 CV of the washing buffer 10 mM histidin, 50 mM NaCl, pH 6. The elution was performed by a gradient from the washing buffer to 10 mM histidin, 50 mM $MgCl_2$, pH 6. The content of Protein S was measured by polyclonal ELISA to 790 ng in the elution pool. The purification was performed at a flow rate of 24 CV/h and at 5° C.

Example 10

Performing Anion Exchange Chromatography at pH 9.0

Anion exchange chromatography was performed at pH 9.0 on a column (0.5 cm in inner diameter×5.5 cm length=1.0 ml column volume (CV)) packed with Amersham Source 30Q, equilibrated with 10 CV 10 mM Tris, 2 mM $CaCl_2$. The load was 8 ml of a solution containing 1 mg/ml FVII and a content of Protein S of more than 10 ppm. The column was washed with 5 CV 10 mM Tris, 2 mM $CaCl_2$. The elution was performed using a 50 CV linear gradient from 0 mM NaCl to 600 mM NaCl, buffered with Tris containing 2 mM $CaCl_2$. Protein S level in collected fractions was evaluated using a Protein S ELISA. Protein S eluted at leading edge of the main peak that contained >99% FVII. The purification was performed at a flow rate of 60 CV/h and at a temperature of 5° C.

C. Hydrophobic Interaction Chromatography

Example 11

Performing Hydrophobic Interaction Chromatography

Hydrophobic interaction chromatography was performed at pH 6.0 on a column (2.6 cm in inner diameter×8.5 cm length=45.1 ml column volume (CV)) packed with Toso Haas TSK-Gel phenyl 5 PW, equilibrated with 10 CV 10 mM citrate, 1.7 M $NH_4$-acetate. The load was 215 ml of a solution containing approximately 700 µg/ml FVII and a content of Protein S of more than 200 ppm. To the load solution 1.7 M $NH_4$-acetate was added. The column was washed with 5 CV 10 mM citrate, 1.7 M $NH_4$-acetate. Elution was performed using a 20 CV linear gradient from 1.7 M $NH_4$-acetate to 0 M NH$_4$-acetate, buffered with citrate. The pool contained a Protein S level below 100 ppm, i.e. a reduction by a factor of at least 2. The purification was performed at a flow rate of 20 CV/h and at a temperature of 5° C.

Example 12

Performing HIC in the Presence of Ca$^{2+}$

Hydrophobic interaction chromatography (HIC) is performed on a column (1 cm inner diameter×7 cm length=5.5 ml) packed with Toyopearl MD-G Butyl resin. The column is equilibrated with 10 CV's of 35 mM CaCl$_2$, 1.5 M NaCl, 10 mM histidine, pH 6.0. After equilibration, 42 ml of a solution containing 0.1 mg/ml FVIIa is loaded onto the column. After loading, the column is washed with 10 CV's of the equilibration buffer. The bound FVII(a) is eluted using 20 mM EDTA, 50 mM histidine, pH 6.0. A FVII(a) containing pool is collected with reduced content of protein S.

D-1. Immunoaffinity Using a Ca$^{2+}$-Dependent Anti-FVIIa Monoclonal Antibodies

Example 13

Performing Immunoaffinity Capture at pH 6

A 1500 ml portion of CHO K1 culture supernatant was stabilized by the addition of calcium to a concentration of 10 mM Ca$^{2+}$ and by the addition of histidine buffer to a concentration of 10 mM, adjusted with HCl to pH 6.0 and filtered through a 0.45 micron dead-end filter. The stabilized culture supernatant was loaded onto a column (1.6 cm inner diameter×10 cm length=20 ml CV) packed with a Ca$^{2+}$-dependent anti-FVIIa monoclonal antibody, immobilized onto Pharmacia Sepharose 4B. Prior to loading, the column was equilibrated with 5 CV's of 10 mM CaCl$_2$, 10 mM histidine, pH 6.0. After loading, the column was washed with 2 M NaCl, 10 mM CaCl$_2$, 10 mM histidine, pH 6.0 for 10 CV's. The bound FVII(a) was eluted with 10 CV's of 30 mM EDTA, 50 mM histidine, pH 6.0. A FVII(a) containing pool was collected from approx. 0.1 AU (280 nm) on the main peak leading edge to approx. 0.1 AU (280 nm) on the tailing edge. A flowrate of 12 CV/h and a temperature of 5° C. were used throughout the purification. Protein S levels were determined by Protein S ELISA, based on polyclonal anti huPS.

D-2. Affinity Purification Using Immobilised Ligands

Example 14

Affinity Purification of a FVII Analogue Using Immobilised Benzamidine Analogues A 1 mL column volume (CV) NHS activated HiTrap (GE Healthcare) was coupled with the benzamidine analogue (Formula 1 or Formula 2). The column was equilibrated with 5 CV of 50 mM HEPES, 100 mM NaCl, 5 mM CaCl$_2$, 0.01% Tween 80, pH 7.5. The column was loaded with 0.5 CV of a solution containing a FVII analogue and 20 mg/L of Protein S, at pH 7.5. After loading the column was washed with 6 CV of equilibration buffer. The elution was performed with 5 CV 50 mM HAc, 100 mM NaCl, 5 mM CaCl$_2$, 0.01% Tween 80, pH 4.4, and 4 CV 50 mM Gly-HCl, 100 mM NaCl, 5 mM CaCl$_2$, 0.01% Tween 80, pH 3.0. The eluate was pH adjusted to pH 6, shortly after elution. The flow rate was 30 CV per hour, and the run was performed at room temperature. The majority of the Protein S did not bind to the resin and was observed in flow through and wash. The opposite was observed for FVII where the majority did bind to the resin and was eluted with decrease in pH. The content of Protein S in the elution fractions was measured by monoclonal ELISA to be about 150 ng and 180 ng using columns immobilised with compound of formula 1 or formula 2, respectively.

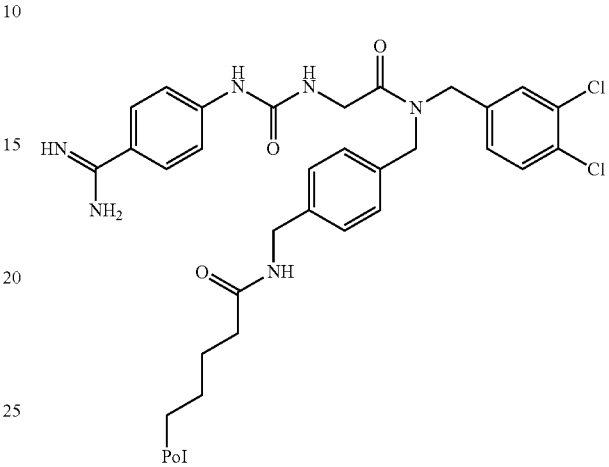

Formula 1

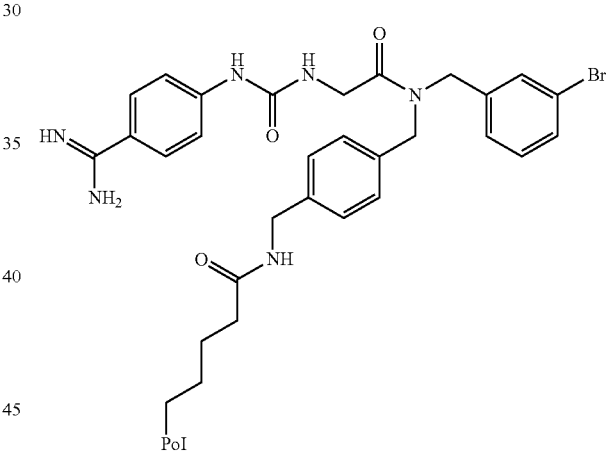

Formula 2

Example 15

Affinity Purification of Protein S Using Immobilised Triazine Ligands (Flow Through Mode)

Purification was performed on a column (1 cm inner diameter×6.2 cm length=5 mL column volume (CV)) packed with ACL 5/5 (ProMetic), equilibrated with 10 CV of 20 mM Tris, 100 mM NaCl, 5 mM CaCl$_2$, pH 8.5. The load was 43 mL of a solution containing more than 40000 ppm of protein S. The column was washed with 2 CV of 20 mM Tris, 100 mM NaCl, 5 mM CaCl$_2$, pH 8.5. The elution was performed using a 40 CV linear gradient from 20 mM Tris, 100 mM NaCl, 5 mM CaCl$_2$, pH 8.5 to 20 mM Tris, 1 M NaCl, 5 mM CaCl$_2$, pH 8.5. A FVII containing pool was collected giving an eluate containing a protein S level below 7000 ppm of protein S.

E. Cation Exchange Chromatography

Example 16

Obelix CIE Cation Exchanger from Amersham Cat No 11-0010

The culture media was loaded on the cation exchange resin. The column was equilibrated with 30 mM NaAc pH 7.0. Flow rate was 48 CV/H at room temperature. After loading, the resin was washed with equilibration buffer followed by washing with 1M NaAc pH 7 for 5-10 column volumes. Equilibration buffer was applied again for 10 column volumes. The product was eluted with 30 mM NaAc, 2M NaCl, pH 6.3 or Tris buffer at higher pH and NaCl. The pool was collected on UV-basis and cooled immediately. Protein S was eluted in the washing steps. The column is cleaned with 1M NaOH after use.

Alternatively, NaAc was added to the application to 1M at pH 7 and washed with the same buffer. Equilibration buffer was 1M NaAc pH 7.0. After application the non-bound material was washed out with equilibration buffer. A wash with 30 mM NaAc pH 6.3 was run for 10 cv and the product was eluted by 30 mM NaAc 2M NaCl pH 6.3 or Tris buffer at higher pH and NaCl. The pool was collected on UV-basis. Protein S elutes in the washing steps.

The resin was also used in the following way: Equilibrated with 30 mM NaAc pH 6.0 and the product (conductivity below 10 mS/cm) applied. Not bound materials were washed out with equilibration buffer and elution was performed by increasing NaCl gradient. Flowrate was 30 cv/h at room temperature. The pool was collected on UV-basis. Protein S was eluted in the front of the product.

Example 17

SP-Sepharose Hp, Amersham Cat No 17-1087

The column was equilibrated with 50 mM Mes, 50 mM NaCl, 2.5 mM $CaCl_2$, pH 5.75. Application was adjusted to conductivity less than 10 mS/cm. Non-bound material was washed out with equilibration buffer and then the product was eluted by increasing the NaCl concentration. Flow rate was 48 column volumes pr hour and the purification done in cold room.

Protein S elutes in the run through fractions. The column was cleaned with 1M NaOH after use.

Example 18

Toyopearl SP 650 M

Reduction of Protein S from a mixture comprising approx. 25 mg/l FVII and 25 mg/l Protein S was performed on a 1 ml (0.5 cm internal diameter×5 cm bed height) Toyopearl SP 650 M (Tosoh Bioscience) column. The column was equilibrated with 10 column volumes (CV) of 10 mM histidine buffer solution, pH 6, and 0.5 ml of the mixture comprising FVII and Protein S was loaded onto the column. The column was washed/eluted with 1 CV of 10 mM histidine buffer solution, pH 6 followed by a gradient wash/elution from 0-1 M NaCl in 10 mM histidine buffer solution, pH 6. The entire purification step was operated at a flow rate of 48 CV/h at room temperature. Protein S was eluted in the flow-through and FVII during the gradient elution. Separation of Protein S and FVII was identified and confirmed by standard, native SDS-PAGE analysis with silver staining and by a parallel purification run loading a FVII standard. The column was equilibrated with 3 CV of 0.1 M NaOH, followed by 10 CV of 1.5 M NaCl+25 mM histidine buffer, pH 6.

Example 19

CM Sepharose FF

Reduction of Protein S from a mixture comprising approx. 25 mg/l FVII and 25 mg/l Protein S was performed on a 1 ml (0.5 cm internal diameter×5 cm bed height) CM Sepharose FF (GE Health Care) column. The column was equilibrated with 10 column volumes (CV) of 40 mM histidine buffer solution, pH 6, and 0.5 ml of the mixture comprising FVII and Protein S was loaded onto the column. The column was washed/eluted with 1 CV of 40 mM histidine buffer solution, pH 6 followed by a gradient wash/elution from 0-0.35 M NaCl in 40 mM histidine buffer solution, pH 6. The entire purification step was operated at a flow rate of 48 CV/h at room temperature. Protein S was eluted in the flow-through and FVII during the gradient elution. Separation of Protein S and FVII was identified and confirmed by standard, native SDS-PAGE analysis with silver staining. The column was equilibrated with 3 CV of 0.1 M NaOH, followed by 10 CV of 1.5 M NaCl+25 mM histidine buffer, pH 6.

Example 20

CM Sepharose FF

Reduction of Protein S from a mixture comprising approx. 25 mg/l FVII and 25 mg/l Protein S was performed on a 1 ml (0.5 cm internal diameter×5 cm bed height) CM Sepharose FF (GE Health Care) column. The column was equilibrated with 10 column volumes (CV) of 10 mM histidine buffer solution, pH 6, and 0.5 ml of the mixture comprising FVII and Protein S was loaded onto the column. The column was washed/eluted with 1 CV of 10 mM histidine buffer solution, pH 6 followed by a gradient wash/elution from 0-0.35 M NaCl in 10 mM histidine buffer solution, pH 6. The entire purification step was operated at a flow rate of 48 CV/h at room temperature. Protein S was eluted in the flow-through and FVII during the gradient elution. Separation of Protein S and FVII was identified and confirmed by standard, native SDS-PAGE analysis with silver staining. The column was equilibrated with 3 CV of 0.1 M NaOH, followed by 10 CV of 1.5 M NaCl+25 mM histidine buffer, pH 6.

Example 21

Toyopearl SP 650 M

Reduction of Protein S from a mixture comprising approx. 25 mg/l FVII and 25 mg/l Protein S was performed on a 1 ml (0.5 cm internal diameter×5 cm bed height) Toyopearl SP 650 M (Tosoh Bioscience) column. The column was equilibrated with 10 column volumes (CV) of 10 mM histidine buffer solution, pH 6, and 0.5 ml of the mixture comprising FVII and Protein S was loaded onto the column. The column was washed/eluted with 1 CV of 10 mM histidine buffer solution, pH 6 followed by a gradient wash/elution from 0-0.35 M NaCl in 10 mM histidine buffer solution, pH 6. The entire purification step was operated at a flow rate of 48 CV/h at room temperature. Protein S was eluted in the flow-through and FVII during the gradient elution. Separation of Protein S and FVII was identified and confirmed by standard, native SDS-PAGE analysis with silver staining. The column was equilibrated with 3 CV of 0.1 M NaOH, followed by 10 CV of 1.5 M NaCl+25 mM histidine buffer, pH 6.

Example 22

Capto MMC

The chromatographic media was packed in a column 1.6 cm in diameter at a bedheight of 10 cm. The purification was carried out at a flowrate of 20 column volumes per hour, at ca. 5° C. The column was equilibrated in 150 mM NaCl, 5 mM $CaCl_2$ and 20 mM histidine, pH 6.0. Culture supernatant comprising FVII was added $CaCl_2$ and histidine to concentrations of 5 and 10 mM respectively, adjusted to pH 6.0, and loaded onto the column. The specific column load was ca. 1.3 mg of FVII pr. mL of packed bed. After load, the column was washed with equilibration buffer, followed by 0.8 M NaCl, 10 mM $CaCl_2$, 20 mM histidine, pH 6.6, followed by equilibration buffer, followed by 0.5 M NaCl, 25 mM histidine, pH 5.8. FVII was eluted from the column with 0.5 M NaCl, 25 mM histidine, pH 6.8. Protein S was found enriched in the flow through during load and in the washing fraction with 0.8 M NaCl, 10 mM $CaCl_2$, 20 mM histidine, pH 6.6.

F. Chromatography Using a Hydroxyapatite Material

Example 23

Hydroxyapatite column, BioRad cat no 157-0085 Type I 80 um

The application is pH adjusted and then applied directly on the resin which is equilibrated before. Flow rate is 42 column volumes pr hour at 4-20 C. Wash out with equilibration buffer (water) until baseline and then elute the product with increasing gradient of $K_2HPO_4/KH_2PO_4$ buffer to 400 mM at pH 6.2. The pool is collected on UV-basis and cooled immediately. Protein S elutes in the back of the product. The column is cleaned with 1M NaOH after use.

G. Heparin Affinity Chromatography

Example 24

Toyopearl Heparin 650 M

Reduction of Protein S from a mixture comprising approx. 25 mg/l FVII and 25 mg/l Protein S was performed on a 1 ml (0.5 cm internal diameter×5 cm bed height) Toyopearl Heparin 650 M (Tosoh Bioscience) column. The column was equilibrated with 10 column volumes (CV) of 10 mM histidine buffer solution, pH 6, and 0.5 ml of the mixture comprising FVII and Protein S was loaded onto the column. The column was washed/eluted with 1 CV of 10 mM histidine buffer solution, pH 6 followed by a gradient wash/elution from 0-0.35 M NaCl in 10 mM histidine buffer solution, pH 6. The entire purification step was operated at a flow rate of 48 CV/h at room temperature. Protein S was eluted before FVII during the gradient elution. Separation of Protein S and FVII was identified and confirmed by standard, native SDS-PAGE analysis with silver staining. The column was equilibrated with 3 CV of 0.1 M NaOH, followed by 10 CV of 1.5 M NaCl+25 mM histidine buffer, pH 6.

The invention claimed is:

1. A method for reducing the concentration of Protein S in a composition comprising a recombinant Vitamin K-dependent protein of interest produced under cell culturing conditions, the method comprising:
   (A) contacting a cell culture supernatant composition comprising a recombinant Vitamin K-dependent protein of interest and Protein S, wherein the recombinant Vitamin K-dependent protein of interest is produced under cell culturing conditions with a chromatographic column comprising a solid phase material carrying monoclonal antibodies against the Vitamin K-dependent protein of interest, wherein the Protein S is present in the composition at an initial concentration of 500 to 1000 parts per million (ppm) relative to the Vitamin K-dependent protein of interest;
   (B) collecting a resulting composition comprising the Vitamin-K dependent protein of interest and Protein S;
   (C) contacting the resulting composition with a chromatographic column comprising a solid phase material carrying monoclonal antibodies against Protein S, wherein the monoclonal antibodies against Protein S selectively bind Protein S but do not bind the recombinant Vitamin K-dependent protein of interest to the solid phase material thereby allowing the Vitamin K-dependent protein of interest to flow through the chromatographic column; and
   (D) collecting the resulting composition comprising the Vitamin-K dependent protein of interest and Protein S, wherein the concentration of Protein S in the resulting composition expressed as parts per million relative to the recombinant Vitamin K-dependent protein of interest is reduced to less than or equal to 100 ppm.

2. The method according to claim 1, wherein the recombinant Vitamin K-dependent protein of interest is human Factor VIIa.

* * * * *